United States Patent [19]

Weinstock

[11] 4,197,297
[45] Apr. 8, 1980

[54] 6-HALO-7,8-DIHYDROXY-1-(HYDROXY-PHENYL)-2,3,4,5-TETRAHYDRO-1H-3-BENZAZEPINES

[75] Inventor: Joseph Weinstock, Phoenixville, Pa.

[73] Assignee: SmithKline Corporation, Philadelphia, Pa.

[21] Appl. No.: 885,823

[22] Filed: Mar. 13, 1978

Related U.S. Application Data

[63] Continuation-in-part of Ser. No. 742,965, Nov. 17, 1976, Pat. No. 4,160,765.

[30] Foreign Application Priority Data

Oct. 4, 1977 [ZA] South Africa ................... 77/5910

[51] Int. Cl.$^2$ ............... A61K 31/55; C07D 223/16
[52] U.S. Cl. ........................... 424/244; 260/239 BB
[58] Field of Search ............... 260/239 BB; 424/244

[56] References Cited

U.S. PATENT DOCUMENTS 3,496,166  2/1970  Mull et al. ................... 260/239 BB

FOREIGN PATENT DOCUMENTS 500194   1/1971   Switzerland ................... 260/239 BB
555831   11/1974  Switzerland ................... 260/239 BB
1225053  3/1971   United Kingdom ............ 260/239 BB Primary Examiner—Alton D. Rollins
Assistant Examiner—D. B. Springer
Attorney, Agent, or Firm—William H. Edgerton

[57] ABSTRACT

6-Halo-7,8-dihydroxy-1-phenyl-2,3,4,5-tetrahydro-1H-3-benzazepines whose structures have a hydroxy group substituted on the 1-phenyl ring have potent and specific antihypertensive activity by means of their peripheral dopaminergic effect. The lead compound of the series is 6-chloro-7,8-dihydroxy-(p-hydroxyphenyl)-2,3,4,5-tetrahydro-1H-3-benzazepine methane sulfonate.

18 Claims, No Drawings

6-HALO-7,8-DIHYDROXY-1-(HYDROXY-PHENYL)-2,3,4,5-TETRAHYDRO-1H-3-BENZAZE-PINES

This application is a continuation-in-part application of copending Ser. No. 742,965 filed Nov. 17, 1976, now U.S. Pat. No. 4,160,765.

This invention concerns a group of compounds whose structures have a 1-phenyl-2,3,4,5-tetrahydro-1H-3-benzazepine skeleton specifically substituted with hydroxy groups at the 7,8-positions, a halo group at the 6-position, no substituent at the 3-position, and a hydroxy group on the 1-phenyl ring. These new compounds are unique antihypertensive agents.

STATEMENT OF THE PRIOR ART

Certain 1-phenyl-2,3,4,5-tetrahydro-1H-3-benzazepines have been described in U.S. Pat. Nos. 3,393,192, 4,052,506, 4,011,319, 3,609,138 and 3,743,731; British Pat. Nos. 1,268,243 and 1,118,688; and Swiss Pat. No. 555,831 including general methods of preparation. However these references disclose no specific benz-trisubstituted compounds, no 6-halo-substituted compounds and no particular biological advantage to the specific substitution pattern present in the structures of the compounds of this invention. British Pat. No. 1,225,053 discloses certain halo-substituted benzazepines not related in structure to those claimed here.

DESCRIPTION OF THE INVENTION

This invention offers a new group of compounds which are 1-phenyl-2,3,4,5-tetrahydro-1H-3-benzazepines having (a) at least three specific substituents in the benz-ring of the nucleus, one of which is a halo or halo-containing group substituted at the 6-position the other two are hydroxy or derivatized hydroxy groups at the 7 and 8-positions, (b) a hydroxy or derivatized hydroxy substituent on the 1-phenyl ring, and (c) no substituent at the 3-position. These compounds have utility as medicinally active compounds especially as cardiovascular and/or diuretic agents due to their peripheral dopaminergic activity. They also demonstrate no or very little activity in animal tests which are known to predict anti-Parkinsonism activity by means of interaction with central dopamine receptors. Generally speaking therefore they have a unique action on the cardiovascular system arising from a potent peripheral dopaminergic mechanism of action and particularly a selective effect within the kidney with increased renal blood flow.

The structures of the compounds of this invention are specifically identified by having a halo, that is, a chloro, bromo, iodo or fluoro or halo-containing substituent such as trifluoromethyl or trifluoroethyl group at the 6-position of the 1-phenyltetrahydro-3-benzazepine system coupled with a 1-(hydroxyphenyl) moiety. Exemplary of this new group of compounds are those represented by the following structural formulas:

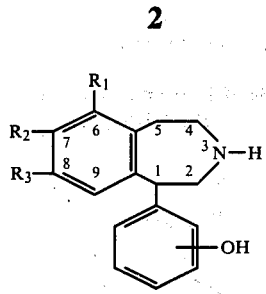

wherein:
$R_1$ is halo or trifluoromethyl; and
$R_2$ and $R_3$ are hydroxy or derivatized hydroxy especially a lower alkanoyloxy of 2–7 carbon atoms such as acetoxy.

The phenolic hydroxy group may be similarly derivatized preferably by the same masking means as the catecholic 7,8-dihydroxy groups. Such compounds may owe their activity to their respective hydroxy parents.

The preferred compound of this invention has the basic structural formula:

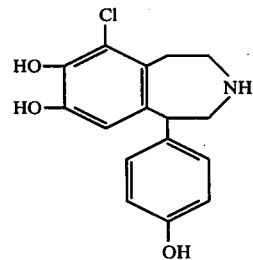

This preferred group of compounds (II) includes salts, esters, metabolic products such as the possible 6-methyl ether or any other derivative which may either directly or indirectly owe its biological activity to the basic compound of Formula II. Such compounds may be isobutyryl, acetyl, butyryl or isoamyl derivatives which may be, for example, metabolized in the body to release the active trihydroxy parent of Formula II.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bis-methylenesalicylic, methanesulfonic ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and especially methanesulfonic acid salts are of particular utility because of good solubility and oral activity.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Specific methods of resolution are disclosed in Swiss Pat. No. 555,831. Unless otherwise specified herein or in the claims, it is intended to include all isomers, whether separated or mixtures thereof. Where isomers are separated, the desired pharmacological activity will usually predominate in one of the isomers however usually the mixture of isomers is used for the purposes of this invention.

The compounds of Formula I are generally prepared from intermediates of the following formula:

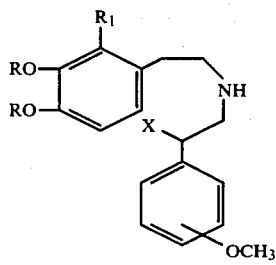

III in which X is hydroxyl or its functional equivalent, R₁ is as defined above, and each R is a lower alkyl especially methyl, benzyl or together are methylene or ethylene; by means of an intramolecular cyclization effected by reaction with a cyclizing agent such as a strong acid for example, trifluoroacetic acid, polyphosphoric acid, sulfuric acid, the preferred sulfuric acid in trifluoroacetic acid, polyphosphoric ester, methanesulfonic acid in methylene chloride or hydrobromic acid as well as a Lewis acid such as boron trifluoride, aluminum chloride or stannic chloride which is able to generate the desired carbonium ion from the substituent X. The term "chemically inert" means under the conditions of the cyclization reaction the substituent is not altered unless of course the operator so desires. For example carrying out the cyclization in 48% hydrobromic acid when R is methyl and the phenyl substituent is methoxy splits the ether links to give the desired hydroxy cyclic compounds but not in the best yields.

The phenethylamines (IV) which are used as starting materials for this method are either known or are prepared by methods described in U.S. Pat. Nos. 3,211,792, 3,804,839, 3,869,474, Chem. Abst. 80, 95398, J. Am. Chem. Soc. 78 4419 (1956) or in the illustrative examples here disclosed.

To prepare the compounds of Formula I where each R is alkanoyloxy, the corresponding 3-benzyl-dihydroxy-3-benzazepine (obtained by N-alkylation of the hydroxy-benzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The alkanoyloxy derivatives such as the important acetoxy compounds can also be prepared by direct O-acylation of the 6-halo-7,8-dihydroxy-1-phenyl-2,3,4,5-tetrahydro-1H-3-benzazepine hydrobromides in trifluoroacetic acid at ambient temperature with the appropriate acyl anhydride or halide.

The intermediates of Formula III above are conveniently prepared by heating equimolar amounts of a styrene oxide with a 3,4-dialkoxy-2-halophenethylamine or by reaction of such a phenethylamine with a blocked bromohydin.

The alternative and preferred blocked bromohydrin method comprises condensing a 2-halo-3,4-lower alkoxyphenethylamine with an O-protected α-phenylbromohydrin. The O-protecting group may be any known to be useful in the art but the isobutyl is preferred. The reaction is most conveniently run in a suitable solvent such as dimethylformamide or dimethylacetamide in the presence of base such as carbonate. Temperatures may run from 75° up to about 125°. The mole ratio is 1 to 1. The O-protective group is then split as known to the art. Details of this method are in the Examples.

The active compounds of this invention used herein specifically stimulate peripheral dopamine receptors. As such they increase renal blood flow and/or decrease renal vascular resistance without a centrally mediated action. As an end result they have a unique biological, and especially hypotensive, activity. No known dopaminergic agents other than dopamine itself are commercially available for the treatment of cardiovascular imbalances. The nonspecific dopaminergic activity of certain specific compounds in the hydroxy-1-phenyl-benzazepine series is described in U.S. Pat. Nos. 4,052,506 and 4,011,319.

The renal vasodilator activity of the benzazepine compounds of Formula I is readily measured in an anesthetized dog. In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors.

A representative but advantageous compound of Formula I, 6-chloro-7,8-dihydroxy-1-(p-hydroxyphenyl)-2,3,4,5-tetrahydro-1H-3-benzazepine hydrobromide tested by i.v. infusion as described above produced an ED₁₅ of 0.3 mcg/kg in five dogs and 0.25 mcg/kg in two dogs with little direct effect on systemic blood pressure in normotensive animals. Such an ED₁₅ therefore is the cumulative dose by infusion which produces a 15% decrease in renal vascular resistance $$(R = \frac{\text{B.P. in mm/kg}}{\text{B.F. ml/min}}).$$

The ED₁₅ of the methane sulfonate salt was 0.94 mcg/kg in six dogs. Therefore the lead compound of the series here claimed (0.3 mcg/kg) is about 10 times as active as its deshydroxy congener, 6-chloro-7,8-dihydroxy-1-phenyl-2,3,4,5-tetrahydro-1H-3-benzazepine hydrobromide (3.5 mcg/kg in two dogs). A s a renal vasodilator in the anesthetized dog the latter 6-chloro deshydroxy compound was in turn 10 times more efficacious than was its 6-deschloro congener. 7,8-Dihydroxy-1-phenyl-2,3,4,5-tetrahydro-1H-3-benzazepine hydrobromide had an ED₁₅ of 80 and 35 mcg/kg each in three dogs. Therefore the lead compound of this invention is at least 100 times as active in this test as in the prior art congener of U.S. Pat. No. 4,011,319.

The 6-chloro-m-hydroxyphenyl congener of this invention had an ED₁₅ of 0.35 mcg/kg in two dogs; the 6-bromo-p-hydroxyphenyl congener, 5 mcg/kg in two dogs which is about twice its deshydroxy congener. The 6-trifluoromethyl congener had less activity.

In addition to the selective renal vasodilator activity effect, the benzazepine compounds of this formula produce weak but significant diuretic activity. Such diuretic activity was measured in the standard rat renal clearance procedure. An increase in renal blood flow was noted with the lead compound but no increase in urine volume of sodium excretion. In rats therefore response to date has been uncertain in one test system however conventional diuretic tests in the dog may be used with significant results.

6-Chloro-7,8-dihydroxy-1-(p-hydroxyphenyl)-2,3,4,5-tetrahydro-1H-3-benzazepine hydrobromide in dimethylsulfoxide/0.9% saline tested in the phosphate mannitol dog produced a significant increase in renal plasma flow at a dose as low as 5 and 10 micrograms, μg/kg/min i.v. Similar results were obtained at oral doses of 10 mg/kg showing a RPF increase of 14, 51 and 54% at phases II, III and IV respectively with very little effect on the glomeralar filtration rate (GFR). The methane sulfonate salt also showed significantly increased RPF at 2.5 mg/kg p.o. at all post-drug phases. 5 mg/kg p.o. gave very significant improvement as did 20 mg/kg p.o.

Some related benzazepine compounds in the prior art such as the deshydroxy congeners mentioned above (see U.S. Pat. No. 4,052,506) also have substantial antiparkinsonism activity due to central dopaminergic activity as demonstrated by employing a modified standard animal pharmacological test procedure reported by Ungerstedt et al., in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate central dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

The advantageous compounds of this invention especially the lead compound 6-chloro-7,8-dihydroxy-1-(p-hydroxyphenyl)-2,3,4,5-tetrahydro-1H-3-benzazepine when tested as described above in rats produced no $ED_{500}$ at substantial doses (10 mg/kg). This demonstrates a lack of activity at the dopaminergic sites in the central nervous system following peripheral administration of the compound which is a unique separation of activity and should give a much lower potential for central nervous system side effects to the compounds of this invention. On the other hand, the deshydroxy congener of my parent application, 6-chloro-dihydroxy-1-phenyl-2,3,4,5-tetrahydro-1H-3-benzazepine had a $RD_{500}$ of 0.3 mg/kg and the deschloro congener of the prior art (U.S. Pat. No. 4,052,506) 7,8-dihydroxy-1-phenyl-2,3,4,5-tetrahydro-1H-3-benzazepine had a $RD_{500}$ of 0.22 mg/kg.

This low potential for centrally controlled side effects has been confirmed by other pharmacological tests following peripheral administration which indeed reveal little CNS activity, a relatively low level of activity at peripheral α- or β-adrenergic receptors and a rather specific action at the kidney rather than other vascular beds and organs. Very large doses cause only a modest effect on heart rate compared to the deshydroxy congener or of course with dopamine itself.

The pharmaceutical compositions of this invention having peripheral dopaminergic activity are prepared in conventional dosage unit forms by incorporating a compound of Formula I, an isomer or a pharmaceutically acceptable acid addition salt or derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 5 mg to about 500 mg preferably about 15–75 mg of active ingredient per dosage unit but this quantity depends on the relative potency of the basic compound, the specific biological activity desired, the route of administration and the conditions of the patient. The lead or preferred compound (II) of this invention especially as the methyl sulfonate salt has been found to have good absorbability from the gastrointestinal tract so oral dosage forms are of prime importance here preferably selected from the dosage unit ranges given above. Intravenous or subcutaneous doses would be lower.

The methods of using the new compounds of this invention for medical purposes manifest themselves in a number of ways. Broadly speaking a peripheral dopaminergic effect is induced in patients in need thereof. The compounds induce an increased renal blood flow. The end result will be an antihypertensive effect on patients having elevated blood pressures or to maintain stabilized blood pressures in patients prone to elevated pressures. This assertion does not rule out that the end result may be partially due to another mechanism of action.

Alternatively since the compounds of this invention are selective peripheral dopaminergic compounds and dopamine itself is useful in the treatment of shock, these compounds such as the lead compound may be used to treat shock in the hospital or treatment room intravenously at dose which will offer from about 10–200 mcg/min of the basic compound to the average human subject. Dopamine itself in the dog test procedure outlined above has an $ED_{15}$ of about 3 mcg/kg/min. In medical practice dopamine has use in various hemodynamic imbalances as noted in the Physicians' Desk Reference 33 566 (1977) but not in a selective manner.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate of glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal oral doses within the ranges given above will be administered several times, such as from two to five times a day with the daily dosage regimen being selected from about 10 mg to about 1.0 g preferably 50–500 mg/kg for oral dosage units. When the method described above is carried out antihypertensive and/or diuretic activity is produced with a minimum of CNS related or cardiac side effects. For an average size human for the preferred species (II) a preferred oral dose to show antihypertensive activity would be selected from the range of from about 15–75 mg for each dosage unit adapted for oral administration to be administered from 2–5 times daily.

The following examples are designed solely to illustrate the preparation and use of the compounds of this invention. The temperatures are centigrade. Other variations of these examples will be obvious to those skilled in the art.

EXAMPLE 1

A mixture of 4.84 g of 50% of sodium hydride in mineral oil and 70 ml of dry dimethylsulfoxide was stirred at 65°–70° for 80 minutes. After dilution with 70 ml of dry tetrahydrofuran, the mixture was cooled to 0° while a solution of 19.0 g (0.093 mole) of trimethylsulfonium iodide in 100 ml of dimethylsulfoxide was added. A solution of 12.6 g (0.0928 mole) of m-anisaldehyde in 40 ml of tetrahydrofuran was quickly added. After stirring for 15 minutes at 0° and 1½ hour at 25°, the mixture is poured into 1½ l. of ice/water slurry and extracted well with water. The combined organic layers were washed with brine, dried and concentrated to give 13 g of crude epoxide. This is mixed with 13.0 g of 2-(2-chloro-3,4-dimethoxyphenyl)ethylamine and heated at 110° for 4 hours. The product was chromatographed over silica gel with 3% methanol/chloroform. The product containing cuts were worked up to give 1.9 g of N-[2-(2-chloro-3,4-dimethoxyphenyl)ethyl]-2-hydroxy-2-(m-methoxyphenyl)ethylamine, m.p. 95.5°–96.5°.

The m-methoxy substituted hydroxyphenethylamine intermediate (1.7 g) in 25 ml of 48% hydrogen bromide solution was heated at 135°–140° for 3 hours. The solvent was evaporated in vacuo and the residue dissolved in methyl alcohol/2-propanol. After charcoal treatment, the solvent was evaporated to leave an amber syrup. This was taken into acetonitrile/2-propanol and a white solid separated by addition of ether. Recrystallization from acetonitrile/ether gave 1.2 g of 6-chloro-7,8-dihydroxy-1-(m-hydroxyphenyl)-2,3,4,5-tetrahydro-1H-3-benzazepine hydrobromide, m.p. 195°–200°.

EXAMPLE 2

2-Chloro-3,4-dimethoxyphenethylamine (1.0 g) was reacted with 0.70 g of p-methoxystyrene oxide as described above to give the hydroxyphenethylamine; m.p. 118.5°–121°. This compound (2.16 g) was stirred at room temperature in 15 ml of trifluoroacetic acid with 4 drops of conc. sulfuric acid. Working up as described gave, after purification over a silica gel column with chloroform, 10% methanol/chloroform as eluates, the desired 6-chloro-7,8-dimethoxy-1-p-methoxyphenyl-2,3,4,5-tetrahydro-1H-3-benzazepine (0.78 g), m.p. 143°–145°.

The trimethoxy product (0.87 g, 2.50 mmoles) in 25 ml of dry methylene chloride was cooled in an ice-methanol bath as 12.5 ml (25.0 mmoles) of boron tribromide in methylene chloride was added dropwise. After stirring for 4 hours, the mixture was cooled in an ice bath while methanol was carefully added to give 0.37 g, after crystallization from methanol/ethylacetate, of 6-chloro-7,8-dihydroxy-1-p-hydroxyphenyl-2,3,4,5-tetrahydro-1H-3-benzazepine hydrobromide, m.p. 215°.

The base was regenerated from the hydrobromide salt using sodium carbonate solution in 85% yield. Treating the base with various acids gave the following salts; dl-tartrate, fumarate, hydrochloride, sulfate, and the most water soluble one, the methanesulfonate, m.p. 272°.

EXAMPLE 3

6-Chloro-7,8-dihydroxyl-1-p-hydroxyphenyl-2,3,4,5-tetrahydro-1H-3-benzazepine hydrobromide (Example 2, 1.0 g) was slurried in 200 ml of trifluoroacetic acid, then 1.29 ml of acetyl bromide was added. The mixture was heated at reflux for 2 hours then stirred for 2 hours. After evaporation to dryness the residue was taken up in benzene and concentrated to give a solid which was recrystallized from ethylacetatehexane to give 6-chloro-7,8-diacetoxy-1-(p-acetoxyphenyl)-2,3,4,5-tetrahydro-1H-3-benzazepine hydrobromide; m.p. 214.5–217°, 0.77 g.

Similarly the isobutyryloxy, propionyloxy, isovaleryloxy, n-butyryloxy, n-heptanoyloxy and other higher derivatives are prepared at the catecholic hydroxy groups or at all three hydroxy sites.

EXAMPLE 4

A mixture of 9.7 g of sodium hydride, 38 g of trimethylsulfonium iodide and 25.2 g (0.185 mol) of o-methoxybenzaldehyde is reacted to give o-methoxystyrene oxide.

A mixture of 34 g of 2-chloro-3,4-dimethoxyphenylethylamine and 28 g of o-methoxystyrene oxide is heated with stirring under argon on a steam bath overnight. Chilling and stirring yields the product N-[2-(2-chloro-3,4-dimethoxyphenyl)-ethyl]-2-hydroxy-2-(2-methoxyphenyl)ethylamine.

A solution of 5 g of the above prepared ethylamine in 35 ml of 48% hydrobromic acid is heated at reflux under argon for two hours. The reaction mixture is evaporated and the hydrobromide salt is converted to the free base using bicarbonate and carbonate to pH 8.5 in water. The aqueous solution is extracted with ethyl acetate, the extract is dried and evaporated to give the free base. The latter is dissolved in methanol and treated with ethereal hydrogen chloride to give 6-chloro-7,8-dihydroxyl-1-(2-hydroxyphenyl)-2,3,4,5-tetrahydro-1H-3-benzazepine hydrochloride.

EXAMPLE 5

Substituting a stoichiometric quantity of 2-fluoro-3,4-dimethoxyphenethylamine in the synthetic procedure of Example 1 gave 6-fluoro-7,8-dimethoxy-1-(1-methoxyphenyl)-2,3,4,5-tetrahydro-1H-3-benzazepine as a yellow oil. Hydrolysis with boron tribromide gave 6-fluoro-7,8-dihydroxy-1-(p-hydroxyphenyl)-2,3,4,5-tetrahydro-1H-3-benzazepine hydrobromide, m.p. 227° (dec.). Substituting appropriate bromo starting material in the methods described herein gave 6-bromo-7,8-dimethoxy-1-(p-methoxyphenyl)-2,3,4,5-tetrahydro-1H-3-benzazepine then hydrolysis with boron tribromide gave 6-bromo-7,8-dihydroxy-1-(p-hydroxyphenyl)-2,3,4,5-tetrahydro-1H-3-benzazepine hydrobromide, m.p. 254° (dec.).

EXAMPLE 6

A solution of 540 g (containing 500 g) of 4-methoxystyrene in 2 l. of methylene chloride was cooled to −10° and 521.2 g of bromine added dropwise keeping the temperature between −5° and −10°. The last drop caused an abrupt change in color and the addition of bromine was stopped. The solvent was immediately removed under vacuum keeping the bath temperature below 35° and feeding the reaction solution in slowly. When the methylene chloride was gone and the warm oil was mixed with 1600 ml (5.5 ml/g product) of hexane to dissolve the remaining product in the evaporation flask and the bulk of the product. This required warming the solution on a steam bath. Charcoal was added, the solution filtered and the resulting pale yellow solution chilled in an ice bath to give 637 g (58.2% based on styrene, 66% based on bromine uptake) of crystals, m.p. 74°–78°. The pure 1-(4-methoxyphenyl)-1,2-dibromoethane melts 80°–81°.

About 100 ml of liquid was distilled from 600 ml of t-butyl alcohol. To the slightly cooled contents were added 15 g of anhydrous powdered magnesium sulfate. The suspension was stirred for 15 minutes and then 100 g of the dibromoethane added. The reaction was refluxed with stirring for 1.5 hours. About 200 ml of methylene chloride was added to the cooled reaction mixture and the solids were removed by filtration. The solids were washed thoroughly with methylene chloride; the washings were combined with the filtrate and concentrated to dryness at 60°. The residue was stirred with 500 ml of pentane and 500 ml of water and the layers separated. The organic layer was washed with 5% sodium bicarbonate, dried and concentrated under vacuum to give 91.7 g (94%) of a tan oil; 2-bromo-1-(t-butoxy)-1-(4-methoxyphenyl)ethane.

A mixture of freshly prepared, undistilled 2-chloro-3,4-dimethoxyphenethylamine (50 g, 0.232 moles), the bromoether (62.4 g, 0.232 moles), powdered anhydrous potassium carbonate (96.1 g, 0.696 moles) and 175 ml sieve-dried dimethyl formamide (3.5 ml/g amine) was stirred and heated to 110° C. for 2 hours, cooled to room temperature, then poured into 1 liter of water. The mixture was extracted with three 250 ml portions of ethyl acetate; the combined extracts are washed three times with 250 ml of saturated brine, dried and concentrated to 109.6 g of viscous tan oil; N-[2-t-butoxy-2-(4-methoxyphenyl)ethyl]-2-(2-chloro-3,4-dimethoxyphenyl)-ethylamine.

The crude t-butyl ether above (109.6 g, 0.232 mole) was heated and stirred on a steam bath with 500 ml of 10% aqueous sulfuric acid for 1 hour. The reaction mixture was made basic with 40% sodium hydroxide with cooling giving a tan semi-solid. Product was extracted into 150 ml of methylene chloride, washed once with 200 ml of water and dried. Removal of the solvent gave a tan solid which was recrystallized from ethanol/petroleum ether (refrigerated); the solid was collected and washed with cold 1:1 ether/petroleum ether. Upon air-drying the solid weighed 45.2 g (53%), m.p. 116°–118°; N-[2-hydroxy-2-(4-methoxyphenyl)ethyl]-2-(2-chloro-3,4-dimethoxyphenyl)ethylamine.

The aminoalcohol (787 g, 2.151 mole) was dissolved in 5900 ml of trifluoroacetic acid (7.5 ml/g), cooled to ambient temperature, and 179 ml (0.227 ml/g of amine, 3.225 mole) of sulfuric acid added slowly with cooling. The cooling was stirred at 25° for 3.5 hours and then 793 g (9.67 mole) of anhydrous sodium acetate added which raised the reaction temperature to 60°. Most of the trifluoroacetic acid was vacuum distilled off keeping the pot temperature <55°. After standing overnight, water was added and the mixture made basic with 14 N ammonium hydroxide with cooling. The mixture was extracted twice with methylene chloride which was then dried and concentrated under vacuum to give a yellow solid. Recrystallization of this from 1900 ml of ethyl acetate gave a solid which was collected and washed with ether. Drying gave 517 g (69%) of crystalline, 6-chloro-7,8-dimethoxy-1-(4-methoxyphenyl)-2,3,4,5-tetrahydro-1H-3-benzazepine, m.p. 140°–142.5°.

The trimethoxybenzazepine (229 g, 0.659 mole) was dissolved in 2290 ml (10 m/lg) of methylenechloride, cooled in an ice bath, and a solution of the boron tribromide in 1 l. of dry methylene chloride added at a rate to maintain the temperature near 15°. A gray-green precipitate formed during the addition. The cooling bath was removed and the reaction mixture stirred at room temperature for 3 hours. The reaction flask was cooled in a dry ice-acetone bath and 1650 ml of methanol added at −20° slowly, giving a brown precipitate. This was warmed to room temperature and the slurry concentrated until most of the solvent was removed and the residue started to foam. The residue was triturated warm with 1 l. of ethyl acetate, cooled, the precipitate collected, washed with ether, and air dried overnight to give 240.7 g (95%) of a light tan solid, m.p. 277° (dec); 6-chloro-7,8-dihydroxy-1-(4-hydroxyphenyl)-2,3,4,5-tetrahydro-1H-3-benzazepine hydrobromide.

The hydrobromide salt (250 g, 0.646 mole) was dissolved in 3500 of methanol with stirring (15 min.). This resultant light orange solution was divided in half and each half added to 2000 ml of 5% sodium bicarbonate solution over 15–20 min. with stirring with the temperature at 25°. The gray slurries were combined, stirred for 30 min., filtered and the filter cake washed with 10 l. of water. The wet gray filter cake which is the free base was slurried in 2 l. of methanol and 50.3 ml(0.775 mole, 20% excess) of methane sulfonic acid added. The mixture is concentrated to dryness at 75°. The off-white solid was triturated with 400 ml boiling of methanol giving a paste to which 1 l. of ethyl acetate is added with vigorous swirling. The slurry was chilled in the refrigerator, filtered, washed with 300 ml ethyl acetate then 300 ml ether. The oven-dried white methanesulfonate salt weighs 220 g (85%), m.p. 272°.

EXAMPLE 7

A mixture of 3.0 g (0.0143 mole) of trifluoroacetic anhydride in 10 ml of methylene chloride was added dropwise to a stirred mixture of 5.0 g (0.0127 mole) of 6-bromo-7,8-dimethoxy-1-(p-methoxyphenyl)-2,3,4,5-tetrahydro-1H-3-benzazepine (prepared as in Example 5) in methylene chloride. After stirring for 1 hour, the solvent was evaporated, methanol was added to the residue and the mixture evaporated again to leave a syrup. This was triturated in ether. The filtrate was evaporated in vacuo. The residue was recrystallized from aqueous ethanol to give the crude N-trifluoroacetyl derivative. Another purification may be optionally carried out.

A mixture of this compound (4.4 g, 0.0090 mole), 0.06 g (0.0360 mole) of trifluoromethyl iodide, 4.5 g (0.0708 mole) of cooper powder in 15 ml of dimethylformamide in a pressure reactor was heated at 150° for 68 hours. After cooling in a dry ice mixture the reactor was opened. The mixture was diluted with 70 ml of dimethylformamide, 200 ml of ethyl acetate, then stirred while 500 ml of water was added. The separated solid was separated and washed with ethyl acetate. The organic phase was separated. The aqueous phase was washed with ethyl acetate. The ethyl acetate extracts were combined, washed with water, brine, dried and evaporated. The residue was 6-trifluoromethyl-7,8-dimethoxy-3-trifluoroacetyl-1-(p-methoxyphenyl)-2,3,4,5-tetrahydro-1H-3-benzazepine. After purification the compound melts at 81°–84°.

Freshly distilled pyridine hydrochloride (1 g) was heated to 210° then 3.50 g (0.00733 mole) of the trimethoxy product added. Heated with stirring for 3 hours. The cooled mixture was taken up in ethyl acetate/water. The organic phase and extracts were combined, washed, dried and evaporated to give 6-trifluoromethyl-7,8-dihydroxy-3-trifluoroacetyl-1-(p-hydroxyphenyl)-2,3,4,5-tetrahydro-1H-3-benzazepine. Purification can be accomplished by chromotography over silica gel and recrystallization from chloroform/petroleum ether.

A mixture of 0.70 g (0.00161 mole) of the N-trifluoroacetyl product in 200 ml of ethanol and 14 ml of 6N hydrochloric acid was heated at reflux for 12 hours. The mixture was evaporated to dryness. The resulting foam was dissolved in absolute ethanol and evaporated several times. The residue was recrystallized from ethyl acetate to give 6-trifluoromethyl-7,8-dihydroxy-1-(p-hydroxyphenyl)-2,3,4,5-tetrahydro-1-H-3-benzazepine hydrochloride as the hydrate, m.p. 189°–180° fused; 223° foamed.

EXAMPLE 8

| Ingredients | Mg. per Capsule |
| --- | --- |
| 6-Chloro-7,8-dihydroxy-1-(p-hydroxyphenyl)-2,3,4,5-tetrahydro-1H-3-benzazepine methane sulfonate | 25 (free base) |
| Magnesium stearate | 2 |
| Lactose | 200 |

The above ingredients are thoroughly mixed and placed into hard gelatin capsules. Such capsules are administered orally to subjects in need of treatment from 2–5 times daily to induce peripheral dopaminergic activity to treat hypertension.

EXAMPLE 9

| Ingredients | Mg. per Tablet |
| --- | --- |
| 6-Chloro-7,8-dihydroxy-1-(p-hydroxyphenyl)-2,3,4,5-tetrahydro-1H-3-benzazepine methane sulfonate | 100 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into scored tablets which can optionally be broken in two for 50 mg dosages.

Sustained release capsules may be prepared by using the methods of U.S. Pat. No. 2,738,303. Of course one such capsule may replace several conventional tablets or capsules.

The capsules or tablets thusly prepared are administered orally to an animal or human requiring stimulation of peripheral dopamine receptors within the dose ranges set forth hereinabove. Similarly other compounds of Formula I and the illustrative examples can be formulated in the same manner to give pharmaceutical compositions useful in the methods of this invention based on their chemical characteristics and relative biological activity using the test methods outlined.

The acute toxicity in mice of the preferred lead compound (II) as the methane sulfonate was 28.9 mg/kg i.v. and 1261 mg/kg p.o. Rats were given the compound in a 5 day dose range orally at doses of 38.1, 76.1, 152.2 and 304.4 mg/kg with weight loss only at the highest two doses. In weekly toxicity tests in beagle dogs emesis was the chief side effect noted at high doses. It will be appreciated the side effects were observed at many times higher than the effective doses.

What is claimed is:
1. A compound of the structural formula:

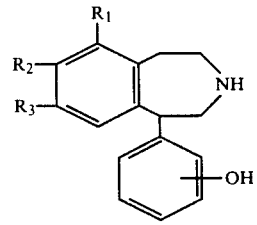

in which:

$R_1$ is halo; and
$R_2$ and $R_3$ are hydroxy;
a nontoxic, pharmaceutically acceptable acid addition salt or a tri-Q-lower alkanoyl ester thereof each of said lower alkanoyl groups having from 2–7 carbon atoms.

2. The compound of claim 1 in which $R_1$ is chloro.

3. The compound of claims 1 or 2 in which $R_2$ and $R_3$ are hydroxy.

4. The compound of claim 1 in which the hydroxy group is at the p-position.

5. The compound of claim 1 being 6-chloro-7,8-dihydroxy-1-(p-hydroxyphenyl)-2,3,4,5-tetrahydro-1H-3-benzazepine or one of its pharmaceutically acceptable acid addition salts.

6. The compound of claim 5 being the free base.

7. The compound of claim 5 being the methane sulfonate salt.

8. The compound of claim 5 being the hydrochloride or hydrobromide salt.

9. The compound of claim 1 being 6-chloro-7,8-dihydroxy-1-(m-hydroxyphenyl)-2,3,4,5-tetrahydro-1H-3-benzazepine or its hydrochloride, hydrobromide or methane sulfonate salts.

10. The method of inducing peripheral dopaminergic activity in a subject in need thereof comprising administering orally or by injection a nontoxic dopaminergic quantity of a compound of claims 1, 5 or 7.

11. The method of inducing antihypertensive activity in a subject in need thereof comprising administering orally or by injection a nontoxic antihypertensive quantity of a compound of claims 1, 5 or 7.

12. The method of claim 11 in which the compound is 6-chloro-7,8-dihydroxy-1-(p-hydroxyphenyl)-2,3,4,5-tetrahydro-1H-3-benzazepine or one of its pharmaceutically acceptable acid addition salts and the route of administration is oral or intravenous.

13. The method of claim 11 in which the compound is 6-chloro-7,8-dihydroxy-1-(p-hydroxyphenyl)-2,3,4,5-tetrahydro-1H-3-benzazepine or one of its pharmaceutically acceptable acid addition salts, the route of administration is oral and the oral dosage unit is selected from the range of about 5–500 mg, of the compound.

14. The method of claim 13 in which the compound is 6-chloro-7,8-dihydroxy-1-(p-hydroxyphenyl)-2,3,4,5-tetrahydro-1H-3-benzazepine methane sulfonate and the oral dosage unit is selected from the range of about 15–75 mg of the compound.

15. The method of inducing antishock activity in a subject in need thereof comprising administering intravenously to said subject a nontoxic antishock quantity of a compound of claims 1, 5 or 7.

16. The method of claim 10 in which said dosage unit is one adapted for oral use and is administered from 2–5 times daily.

17. The pharmaceutical composition having antihypertension activity due to a peripheral dopaminergic mechanism comprising a nontoxic anti-hypertensive quantity of a compound of claims 1, 5 or 7 combined with a pharmaceutical carrier.

18. The composition of claim 17 in which the compound is 6-chloro-7,8-dihydroxy-1-(p-hydroxyphenyl)-2,3,4,5-tetrahydro-1H-3-benzazepine methanesulfonate, the composition is an oral dosage unit and the quantity of compound is selected from the range of from 15–75 mg.

* * * * *

UNITED STATES PATENT AND TRADEMARK OFFICE

BEFORE THE COMMISSIONER OF PATENTS AND TRADEMARKS

In re SmithKline Beecham Corporation  :
Request for Patent Term Extension     :  ORDER GRANTING
U.S. Patent No. 4,197,297             :  INTERIM EXTENSION On March 21, 1997, Neurex Corporation, an agent of SmithKline Beecham Corporation, the owner of record of U.S. Patent No. 4,197,297, filed an application under 35 U.S.C. § 156(d)(5) for interim extension of the term of U.S. Patent No. 4,197,297. The patent claims the active ingredient, fenoldopam mesylate, in the human drug product "CORLOPAM®" and methods of use of said active ingredient. The application indicates, and the Food and Drug Administration (FDA) has confirmed, that the product is currently undergoing a regulatory review under Section 505 of the Federal Food, Drug, and Cosmetic Act (21 U.S.C. § 355) before the FDA for permission to market or use the product commercially. The original term of the patent expires on April 8, 1997.

Review of the application indicates that, except for permission to market or use the product commercially, the subject patent would be eligible for an extension of the patent term under 35 U.S.C. § 156. Since it is apparent that the regulatory review period may extend beyond the date of expiration of the patent, interim extension of the patent term under 35 U.S.C. § 156(d)(5) is appropriate.

An interim extension under 35 U.S.C. § 156(d)(5) of the term of U.S. Patent No. 4,197,297 is granted for a period of one year from the original expiration date of the patent.

APR - 7 1997
Date

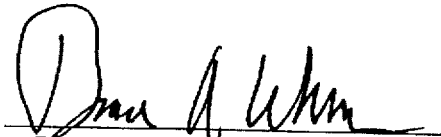

Bruce A. Lehman
Assistant Secretary of Commerce and
Commissioner of Patents and Trademarks